United States Patent
Christensen, IV et al.

(10) Patent No.: US 6,852,882 B2
(45) Date of Patent: Feb. 8, 2005

(54) PEPTIDE DEFORMYLASE INHIBITORS

(75) Inventors: Siegfried B. Christensen, IV, Collegeville, PA (US); Maxwell D. Cummings, Strafford, PA (US); Joseph M. Karpinski, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/478,620

(22) PCT Filed: Jun. 4, 2002

(86) PCT No.: PCT/US02/17697
§ 371 (c)(1),
(2), (4) Date: Nov. 17, 2003

(87) PCT Pub. No.: WO02/098901
PCT Pub. Date: Dec. 12, 2002

(65) Prior Publication Data
US 2004/0157916 A1 Aug. 12, 2004

Related U.S. Application Data
(60) Provisional application No. 60/295,963, filed on Jun. 5, 2001.

(51) Int. Cl.$^7$ .................. C07C 259/04; A61K 31/19
(52) U.S. Cl. .................. 562/621; 562/623; 562/624; 549/72; 514/575; 514/448
(58) Field of Search ................ 562/621, 623, 562/624; 549/72; 514/448, 575

(56) References Cited

U.S. PATENT DOCUMENTS
6,462,042 B1   10/2002   Owen et al.

*Primary Examiner*—Shailendra Kumar
(74) *Attorney, Agent, or Firm*—Soma G. Simon; Mary E. McCarthy; Charles M. Kinzig

(57) ABSTRACT

Novel PDF inhibitors and novel methods for their use are provided.

5 Claims, No Drawings

PEPTIDE DEFORMYLASE INHIBITORS

This application is the National Stage of International Application No. PCT/US02/17697 filed Jun. 4, 2002, which claims the benefit of U.S. Provisional Application No. 60/295,963, filed Jun. 5, 2001.

FIELD OF THE INVENTION

The present invention relates to the use of novel antibacterial compounds, and pharmaceutical compositions containing these compounds as peptide deformylase inhibitors.

BACKGROUND OF THE INVENTION

Bacterial initiator methionyl tRNA is modified by methionyl tRNA formyltransferase (FMT) to produce formyl-methionyl tRNA. The formyl methionine (f-Met) is then incorporated at the N-termini of newly synthesized polypeptides. Polypeptide deformylase (PDF or Def) then deformylates primary translation products to produce N-methionyl polypeptides. Most intracellular proteins are further processed by methionine amino peptidase (MAP) to yield the mature peptide and free methionine, which is recycled. PDF and MAP are both essential for bacterial growth, and PDF is required for MAP activity. This series of reactions is referred to as the methionine cycle (FIG. 1)

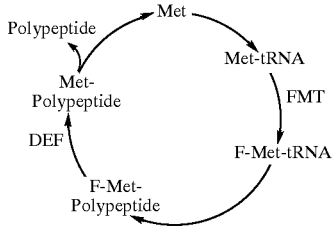

FIG. 1.
The methionine cycle.

To date, polypeptide deformylase homologous genes have been found in bacteria, in chloroplast-containing plants, in mice and in human. The plant proteins are nuclear encoded but appear to carry a chloroplast localization signal. This is consistent with the observation that chloroplast RNA and protein synthesis processes are highly similar to those of eubacteria. No information on protein expression of mammalian PDF gene homologs or functional role for such proteins has been demonstrated to date (Meinnel T. 2000, Parasitology Today, 16(4), 165–168).

Polypeptide deformylase is found in all eubacteria for which high coverage genomic sequence information is available. Sequence diversity among PDF homologs is high, with as little as 20% identity between distantly related sequences. However, conservation around the active site is very high, with several completely conserved residues, including one cysteine and two histidines which are required to coordinate the active site metal (Meinnel, T. et al, 1997, Journal of Molecular Biology, 267, 749–761).

PDF is recognized to be an attractive anti-bacterial target, as this enzyme has been demonstrated to be essential for bacterial growth in vitro (Mazel, D. et al, EMBO J. 13 (4), 914–923, 1994), is not involved in eukaryotic protein synthesis (Rajagopalan et al, J. Am. Chem. Soc. 119, 12418–12419, 1997), and is universally conserved in prokaryotes (Kozak, M. Microbiol. Rev. 47, 1–45, 1983). Therefore PDF inhibitors can potentially serve as broad spectrum anti-bacterial agents.

SUMMARY OF THE INVENTION

The present invention involves novel N-[2-(N-formyl-N-hydroxy-amino)-ethyl]-arylamides with bacterial polypeptide deformylase inhibiting activity represented by Formula (I) hereinbelow and their use as PDF inhibitors.

The present invention further provides methods for inhibiting PDF in an animal, including humans, which comprises administering to a subject in need of treatment an effective amount of a compound of Formula (I) as indicated hereinbelow.

DETAILED DESCRIPTION OF THE INVENTION

The compounds useful in the present methods are selected from Formula (I) hereinbelow:

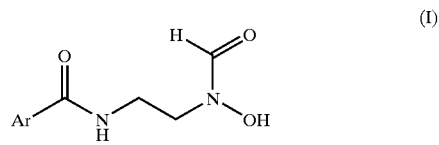

(I)

wherein:
Ar is an aryl group selected from the group consisting of phenyl, azaindolyl, pyridyl, indolyl, quinolinyl, pyrazinyl, benzenethiophenyl, isoxazolyl, isoquinolinyl, napthyl, oxazolyl, isothiazolyl, benzothiaphenyl, furyl, pyridazinyl, thienyl, benzofuryl, triazolyl, imidazolyl, and thiazolyl; such that Ar may be optionally substituted with one, two, or three substituents selected from the group consisting of optionally substituted alkyl or cycloalkyl of one to nine carbons, halo, alkoxy of one to nine carbons, hydroxy, amino, hydroxyalkyl of one to nine carbons, alkoxyalkyl, wherein the alkyl and alkylene groups are independently of one to nine carbons, optionally substituted aryl or optionally substituted heteroaryl, carboxy, and alkoxycarbonyl.

As used herein, "alkyl" refers to an optionally substituted hydrocarbon group joined together by single carbon-carbon bonds. The alkyl hydrocarbon group may be linear, branched or cyclic, saturated or unsaturated.

As used herein, "aryl" refers to an optionally substituted aromatic group with at least one ring having a conjugated pi-electron system, containing up to two conjugated or fused ring systems. "Aryl" includes carbocyclic aryl, heterocyclic aryl and biaryl groups, all of which may be optionally substituted.

Preferred compounds useful in the present invention are selected from the group consisting of:
3,4-Dichloro-N-[2-(N-formyl-N-hydroxy-amino)-ethyl]-benzamide;
3-Trifluoromethyl-N-[2-(N-formyl-N-hydroxy-amino)-ethyl]-benzamide;
2-Methoxy-N-[2-(N-formyl-N-hydroxy-amino)-ethyl]-benzamide;
N-[2-(N-Formyl-N-hydroxy-amino)-ethyl]-thiophen-2-yl-carboxamide;
N-[2-(N-Formyl-N-hydroxy-amino)-ethyl]-thiophen-3-yl-carboxamide;
N-[2-(N-Formyl-N-hydroxy-amino)-ethyl]-benzamide;
3-Chloro-N-[2-(N-formyl-N-hydroxy-amino)-ethyl]-thiophen-2-yl-carboxamide;
5-Chloro-N-[2-(N-formyl-N-hydroxy-amino)-ethyl]-thiophen-2-yl-carboxamide;
3,5-Dichloro-N-[2-(N-formyl-N-hydroxy-amino)-ethyl]-benzamide;

3-Chloro-2-fluoro-5-trifluoromethyl-N-[2-(N-formyl-N-hydroxy-amino)-ethyl]-benzamide;
2-Chloro-5-trifluoromethyl-N-[2-(N-formyl-N-hydroxy-amino)-ethyl]-benzamide;
3-Phenoxy-N-[2-(N-formyl-N-hydroxy-amino)-ethyl]-benzamide;
2,6Dichloro-N-[2-(N-formyl-N-hydroxy-amino)-ethyl]-benzamide;
6-Methoxy-2,3,5-trichloro-N-[2-(N-formyl-N-hydroxy-amino)-ethyl]-benzamide;
5-Phenoxy-2-chloro-N-[2-(N-formyl-N-hydroxy-amino)-ethyl]-benzamide;
2-Chloro-5-phenoxybenzoic acid;
2-Chloro-5-benzyloxy-N-[2-(N-formyl-N-hydroxy-amino)-ethyl]-benzamide;
2-Chloro-5-methoxy-N-[2-(N-formyl-N-hydroxy-amino)-ethyl]-benzamide;
2-Chloro-5-hydroxy-N-[2-(N-formyl-N-hydroxy-amino)-ethyl]-benzamide;
6-Hydroxy-2,3,5-trichloro-N-[2-(N-formyl-N-hydroxy-amino)-ethyl]-benzamide; and
5-Chloro-4-[2-(N-formyl-N-hydroxy-amino)-ethyl]amido-benzimidazole.

More preferred compound useful in the present invention are selected from the group consisting of:
2,3-Dichloro-N-[2-(N-formyl-N-hydroxy-amino)-ethyl]-benzamide;
2,3,5-Trichloro-N-[2-(N-formyl-N-hydroxy-amino)-ethyl]-benzamide;
2,5-Dichloro-N-[2-(N-formyl-N-hydroxy-amino)-ethyl]-benzamide; and
5-Bromo-2-chloro-N-[2-(N-formyl-N-hydroxy-amino)-ethyl]-benzamide.

Also included in the present invention are pharmaceutically acceptable salts and complexes. Preferred are the hydrochloride, hydrobromide and trifluoroacetate salts. The compounds of the present invention may contain one or more asymmetric carbon atoms and may exist in racemic and optically active forms. All of these compounds and diastereomers are contemplated to be within the scope of the present invention.

The compounds and processes of the present invention will be better understood in connection with the following synthetic schemes, which are merely illustrative of the methods by which the compounds of the invention may be prepared and are not intended to limit the scope of the invention as defined in the appended claims.

Compounds of the formula (I) may be prepared according to the Scheme 1.

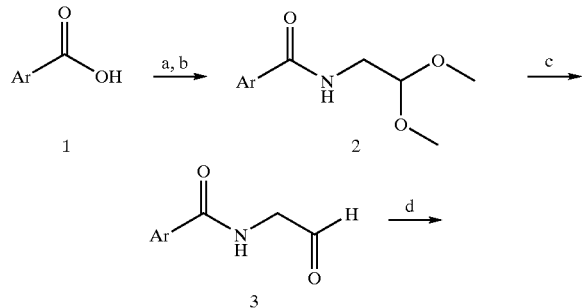

Scheme 1

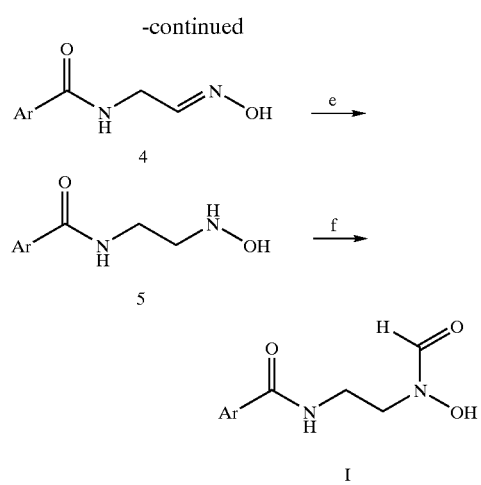

a) (COCl)$_2$, DMF, DCM;
b) aminoacetaldehyde dimethyl acetal, TEA, DCM 0° C.;
c) THF, 6N HCl;
d) NH$_2$OH•HCl, NaOAc, MeOH;
e) NaCNBH$_3$, HCl, MeOH, 0°C;
f) HCO$_2$C(O)CH$_3$, pyridine, 0° C.

Aryl carboxylic acids (1) may be purchased or prepared by standard literature procedures. Conversion of (1) to the acid chloride and amination with the dimethyl acetal of aminoacetaldehyde provides the amide (2). Deprotection with 6NHCl in THF and treatment of the resulting aldehyde (3) with hydroxylamine and sodium acetate in MeOH provides the oxime (4). Reduction of the oxime to the hydroxylamine (5) is accomplished with NaCNBH$_3$ in MeOH under acidic conditions. Finally, N-formyl-N-hydroxylamine (I) is obtained by treatment of the hydroxylamine in pyridine with the mixed anhydride formed from formic acid and acetic anhydride.

The foregoing may be better understood by reference to the following Examples which illustrate the methods by which the compounds of the invention may be prepared and are not intended to limit the scope of the invention as defined in the appended claims.

EXAMPLE 1

Preparation of 2,3-Dichloro-N-[2-(N-formyl-N-hydroxy-amino)-ethyl]-benzamide a). 2,3-Dichloro-N-(2,2-dimethoxy-ethyl)-benzamide To a solution of 2,3-dichlorobenzoic acid (27.5 g, 0.14 mol) in dichloromethane (400 ml) was added oxalyl chloride (0.14 mol, 12.6 mL) and DMF (0.2 mL). The reaction mixture was stirred for 3 h and the resulting 2,3-dichlorobenzoyl chloride was cooled to 0° C.

A mixture of aminoacetaldehyde dimethyl acetal (0.14 mol, 15.7 mL) and triethylamine (0.32 mol, 44.2 mL) in dichloromethane (150 mL) was added to the above acid chloride over 0.25 h. The mixture was stirred an additional 0.3 h, was washed with water (300 mL), with cold 1N HCl (600 mL) and was dried (MgSO$_4$) and was concentrated to provide the title compound (40 g, 100%) as a clear, pale brown oil. $^1$H NMR (400 MHz, CDCl$_3$) δ 7.59 (d, j=1.6 Hz, 1H); 7.38 (m, 2H); 4.50 (t, j=5.1 Hz, 1H); 3.63 (t, j=5.4 Hz, 2H); 3.45 (s, 6H).

b). 2,3-Dichloro-N-(2-oxo-ethyl)-benzamide

A solution of 2,3-dichloro-N-(2,2-dimethoxy-ethyl)-benzamide (40 g, 0.14 mol) in THF (500 ml) and 6N HCl (500 mL) was stirred for 1.5 h. The THF was removed in vacuo, brine (200 mL) was added and the reaction was extracted (4×100 mL) with dichloromethane/MeOH (9:1).

The combined organic extracts were dried (MgSO$_4$) and were concentrated to provide the title compound (33 g, 100%) as a clear, pale brown oil. $^1$H NMR (400 MHz, CDCl$_3$) δ 9.75 (s, 1H); 7.58–7.25 (m, 3H); 4.42 (d, j=4.8 Hz, 2H).

c). 2,3-Dichloro-N-(2-hydroxyimino-ethyl)-benzamide

To a solution of 2,3-dichloro-N-(2-oxo-ethyl)-benzamide (33 g, 0.14 mol) in MeOH (500 mL) was added hydroxylamine hydrochloride (20 g, 0.28 mol) and sodium acetate (23.6 g, 0.28 mol). The mixture was stirred 1.5 h and the MeOH was removed in vacuo. The residue was partioned between saturated NaHCO$_3$ (200 mL) and dichloromethane/MeOH (9:1; 100 mL). The aqueous layer was extracted (4×100 mL) with dichloromethane/MeOH (9:1). The combined organic extracts were washed with brine (50 mL), were dried (Na$_2$SO$_4$) and were concentrated to provide the title compound (34.3 g, 96%) as a 1:1 mixture of cis and trans isomers as a clear, pale brown oil. $^1$H NMR (400 MHz, CD$_3$OD): δ 7.66 (m, 1H); 7.45 (m, 3H); 6.78 (t, j=4.1 Hz, 0.5H); 4.30 (d, j=4.1 Hz, 1H); 4.12 (d, j=5.3 Hz, 1H).

d). 2,3-Dichloro-N-(2-hydroxyamino-ethyl)-benzamide

To a solution of 2,3-dichloro-N-(2-hydroxyimino-ethyl)-benzamide (34.3 g, 0.14 mol) in MeOH (700 mL) under an argon atmosphere at 0° C. was added methyl orange (0.01 g) followed by a saturated solution of MeOH/HCl until a persistent red color was observed. Sodium cyanoborohydride (10.5 g, 0.17 mol) was added sequentially with saturated MeOH/HCl over 0.5 h. The reaction mixture was stirred an additional 1 h and the MeOH was removed in vacuo. The residue was partitioned between 3N HCl (300 mL) and dichloromethane (300 mL). The organic phase was extracted with 3N HCl (2×200 mL). The combined aqueous extracts were washed with dichloromethane, were basidified with cold dilute NaOH and were extracted (7×100 mL) with dichloromethane/MeOH (9:1). The combined organic extracts were washed with brine, were dried (Na$_2$SO$_4$) and were concentrated. The residue was diluted with ether (200 mL) and the precipitate collected by filtration to provide the title compound (11 g, 32%) as a white solid. $^1$H NMR (400 MHz, CD$_3$OD): δ 7.60 (dd, j=1.7 and 7.8 Hz, 1H); 7.41 (dd, j=1.7 and 7.6 Hz, 1H); 7.35 (t, j=7.7 Hz, 1H); 3.57 (t, j=6.2 Hz, 2H); 3.06 (t, j=6.2 Hz, 1H).

e). 2,3-Dichloro-N-[2-(N-formyl-N-hydroxy-amino)-ethyl]-benzamide

A mixture of acetic anhydride (5 mL) and formic acid (2.5 mL) was allowed to stand at 55° C. for 2.5 h. After cooling to 0° C., the resulting mixed anhydride was added to a solution of 2,3-dichloro-N-(2-hydroxyamino-ethyl)-benzamide (10.5 g, 42 mmol) in pyridine (50 mL) at 0° C. under an argon atmosphere. The reaction mixture was stirred for 2 h and the pyridine was removed in vacuo. The residue was chased three times with water and three times with MeOH. The residue was partitioned between cold brine/1N HCl and dichloromethane/MeOH (9:1). The aqueous layer was extracted (10×100 mL) with dichloromethane/MeOH (9:1). The combined organic extracts were dried (Na$_2$SO$_4$) and were concentrated. Purification by preparative reverse-phase HPLC provided the title compound (1.8 g, 15%) as a white solid. $^1$H NMR* (400 MHz, CD$_3$OD): δ 8.35 (s, 0.5H); 7.95 (s, 0.5H); 7.60 (m, 1H); 7.35 (m, 2H); 3.79 (m, 1H); 3.73 (m, 1H); 3.62 (m, 2H). * 1:1 mixture of rotamers. ESMS: M+H=277.

EXAMPLE 2

Preparation of 2,3,5-Trichloro-N-[2-(N-formyl-N-hydroxy-amino)-ethyl]-benzamide a). 2,3,5-Trichloro-N-(2,2-dimethoxy-ethyl)-benzamide To a solution of 2,3,5-trichlorobenzoic acid (0.68 g, 3 mmol) in dichloromethane (20 ml) was added oxalyl chloride (3 mmol, 0.26 mL) and DMF (0.01 mL). The reaction mixture was stirred for 3 h and the resulting 2,3,5-trichlorobenzoyl chloride was cooled to 0° C.

A mixture of aminoacetaldehyde dimethyl acetal (3 mmol, 0.33 mL) and triethylamine (6 mmol, 0.84 mL) in dichloromethane (10 mL) was added to the above acid chloride over 0.25 h. The mixture was stirred an additional 1 h, was washed with water and with cold 1N HCl, was dried (MgSO$_4$) and was concentrated to provide the title compound (0.94 g, 100%) as a white solid. ESMS: M+H=312.

b). 2,3,5-Trichloro-N-(2-oxo-ethyl)-benzamide

A solution of 2,3,5-trichloro-N-(2,2-dimethoxy-ethyl)-benzamide (0.94 g, 3.0 mmol) in THF (40 ml) and 6N HCl (40 mL) was stirred for 18 h. The THF was removed in vacuo, brine (50 mL) was added and the reaction was extracted (4×25 mL) with dichloromethane/MeOH (9:1). The combined organic extracts were dried (MgSO$_4$) and were concentrated to provide the title compound (0.80 g, 100%) as a white wax. $^1$H NMR (400 MHz, CDCl$_3$) δ 9.75 (s, 1H); 7.75 (s, 1H); 7.47 (s, 1H); 4.42 (d, j=4.7 Hz, 2H).

c). 2,3,5-Trichloro-N-(2-hydroxyimino-ethyl)-benzamide

To a solution of 2,3,5-trichloro-N-(2-oxo-ethyl)-benzamide (0.80 g, 3.0 mmol) in MeOH (100 mL) was added hydroxylamine hydrochloride (0.41 g, 6 mmol) and sodium acetate (0.49 g, 6 mmol). The mixture was stirred 18 h and the MeOH was removed in vacuo. The residue was dried in vacuo for 18 h and was used without further purification to yield the title compound (1.4 g) as a white solid. ESMS: M+H=281.

d). 2,3,5-Trichloro-N-(2-hydroxyamino-ethyl)-benzamide

To a solution of 2,3,5-trichloro-N-(2-hydroxyimino-ethyl)-benzamide (0.85 g, 3.0 mmol ) in MeOH (50 mL) under an argon atmosphere at 0° C. was added methyl orange (trace) followed by a saturated solution of MeOH/HCl until a persistent red color was observed. Sodium cyanoborohydride (0.23 g, 3.65 mmol) was dissolved in MeOH (5 mL) was added sequentially with saturated MeOH/HCl over 0.5 h. The reaction mixture was stirred an additional 1 h and the MeOH was removed in vacuo. The residue was basidified with 10% NaOH and extracted (4×25 mL) with dichloromethane/MeOH (9:1). The combined organic extracts were washed with brine, were dried (NaHCO$_3$) and were concentrated. The residue was diluted with ether/MeOH (9:1) and the precipitate was collected to provide the title compound (0.27 g, 32%) as a white solid. ESMS: M+H=283.

e). 2,3,5-Trichloro-N-[2-(N-formyl-N-hydroxy-amino)-ethyl]-benzamide

A mixture of acetic anhydride (2 mL) and formic acid (1 mL) was allowed to stand at 55° C. for 2.5 h. After cooling to 0° C., the resulting mixed anhydride (0.5 mL) was added to a solution of 2,3,5-trichloro-N-(2-hydroxyamino-ethyl)-benzamide (0.27 g, 1.0 mmol) in pyridine (10 mL) at 0° C. under an argon atmosphere. The reaction mixture was stirred for 2 h at room temperature and the pyridine removed in vacuo. The residue was purified by preparative reverse-phase HPLC to provide the title compound (0.09 g, 28%) as a white solid. $^1$H NMR* (400 MHz, CD$_3$OD): δ 8.35 (s, 0.5H); 7.95 (s, 0.5H); 7.70 (s, 1H); 7.42 (s, 1H); 3.78 (m, 1H); 3.73 (m, 1H); 3.60 (m, 2H). * 1:1 mixture of rotamers. ESMS: M+H=311.

EXAMPLE 3

Preparation of 2,5-Dichloro-N-[2-(N-formyl-N-hydroxy-amino)-ethyl]-benzamide a). 2,5-Dichloro-N-(2,2-dimethoxy-ethyl)-benzamide To a solution of 2,5-dichlorobenzoic acid (0.57 g, 3 mmol) in dichloromethane (20 ml) was added oxalyl chloride (3 mmol, 0.26 mL) and DMF (0.01 mL). The reaction mixture was stirred for 3 h and the resulting 2,5-dichlorobenzoyl chloride was cooled to 0° C.

A mixture of aminoacetaldehyde dimethyl acetal (3 mmol, 0.33 mL) and triethylamine (6 mmol, 0.84 mL) in dichloromethane (10 mL) was added to the above acid chloride over 0.25 h. The mixture was stirred an additional 1 h, was washed with water and with cold 1N HCl, was dried (MgSO$_4$) and was concentrated to provide the title compound (0.81 g, 98%) as a pale yellow solid. $^1$H NMR (400 MHz, CDCl$_3$) δ 7.64 (d, j=1.3 Hz, 1H); 7.34 (s, 2H); 6.41 (brs, 1H); 4.51 (t, j=5.3 Hz, 1H); 3.61 (t, j=5.6 Hz, 2H); 3.43 (s, 6H).

b). 2,5-Dichloro-N-(2-oxo-ethyl)-benzamide

A solution of 2,5-dichloro-N-(2,2-dimethoxy-ethyl)-benzamide (0.81 g, 2.9 mmol) in THF (40 ml) and 6N HCl (40 mL) was stirred for 18 h. The THF was removed in vacuo, brine (50 mL) was added and the reaction was extracted (4×25 mL) with dichloromethane/MeOH (9:1). The combined organic extracts were dried (MgSO$_4$) and were concentrated to provide the title compound (0.67 g, 100%) as a clear, pale yellow oil. 1H NMR (400 MHz, CDCl$_3$) δ 9.75 (s, 1H), 7.45–7.38 (m, 3H), 4.42 (d, j=4.7 Hz, 2H).

c). 2,5-Dichloro-N-(2-hydroxyimino-ethyl)-benzamide

To a solution of 2,5-dichloro-N-(2-oxo-ethyl)-benzamide (0.67 g, 2.9 mmol) in MeOH (100 mL) was added hydroxylamine hydrochloride (0.41 g, 5.8 mmol) and sodium acetate (0.48 g, 5.8 mmol). The mixture was stirred 18 h and the MeOH was removed in vacuo. The residue was dried in vacuo for 18 h and used without further purification to provide the title compound (1.34 g) as a white solid. ESMS: M+H=247.

d). 2,5-Dichloro-N-(2-hydroxyamino-ethyl)-benzamide

To a solution of 2,5-dichloro-N-(2-hydroxyimino-ethyl)-benzamide (0.72 g, 2.9 mmol) in MeOH (20 mL) under an argon atmosphere at 0° C. was added methyl orange (trace) followed by a saturated solution of MeOH/HCl until a persistent red color was observed. Sodium cyanoborohydride (0.22 g, 3.5 mmol) was dissolved in MeOH (5 mL) and was added sequentially with saturated MeOH/HCl over 0.5 h. The reaction mixture was stirred an additional 1 h and the MeOH was removed in vacuo. The residue was basidified with saturated Na$_2$CO$_3$ and extracted (7×25 mL) with dichloromethane/MeOH (9:1). The combined organic extracts were washed with brine, were dried (Na$_2$SO$_4$) and were concentrated. The residue was purified by flash chromatography (2%–5% MeOH/dichloromethane) to provide the title compound (0.29 g, 40%) as a white solid. $^1$H NMR (400 MHz, CD$_3$OD): δ 7.53 (s, 1H); 7.44 (s, 2H); 3.56 (t, j=6.2 Hz, 2H); 3.06 (t, j=6.2 Hz, 2H). ESMS: M+H=249.

e). 2,5-Dichloro-N-[2-(N-formyl-N-hydroxy-amino)-ethyl]-benzamide

A mixture of acetic anhydride (2 mL) and formic acid (1 mL) was allowed to stand at 55° C. for 2.5 h. After cooling to 0° C., the resulting mixed anhydride (0.4 mL) was added to a solution of 2,5-dichloro-N-(2-hydroxyamino-ethyl)-benzamide (0.28 g, 1.1 mmol) in pyridine (10 mL) at 0° C. under an argon atmosphere. The reaction mixture was stirred for 2 h and the pyridine removed in vacuo. The residue was purified by preparative reverse-phase HPLC to provide the title compound (0.1 g, 33%) as a white solid. $^1$H NMR* (400 MHz, CD$_3$OD): δ 8.35 (s, 0.5H); 7.95 (s, 0.5H); 7.45 (m, 3H); 3.78 (m, 1H); 3.73 (m, 1H); 3.62 (m, 2H). * 1:1 mixture of rotamers. ESMS: M+H=277.

EXAMPLE 4

Preparation of 5-Bromo-2-chloro-N-[2-(N-formyl-N-hydroxy-amino)-ethyl]-benzamide a). 5-Bromo-2-chloro-N-(2,2-dimethoxy-ethyl)-benzamide To a solution of 5-bromo-2-chlorobenzoic acid (10 g, 42.5 mmol) in dichloromethane (400 ml) was added oxalyl chloride (42.5 mmol, 3.7 mL) and DMF (0.05 mL). The reaction mixture was stirred for 3 h and the resulting 5-bromo-2-chlorobenzoyl chloride was cooled to 0° C.

A mixture of aminoacetaldehyde dimethyl acetal (42.5 mmol, 4.63 mL) and triethylamine (93.5 mmol, 13 mL) in dichloromethane (50 mL) was added to the above acid chloride over 0.25 h. The mixture was stirred an additional 1 h, was washed with water and with cold 1N HCl, was dried (MgSO$_4$) and was concentrated to provide the title compound (13.7 g, 100%) as a pale yellow solid. ESMS: M+H=322.

b). 5-Bromo-2-chloro-N-(2-oxo-ethyl)-benzamide

A solution of 5-bromo-2-chloro-N-(2,2-dimethoxy-ethyl)-benzamide (13.7 g, 42.5 mmol) in THF (250 ml) and 6N HCl (150 mL) was stirred for 18 h. The THF was removed in vacuo, brine (200 mL) was added and the reaction was extracted (4×100 mL) with dichloromethane/MeOH (9:1). The combined organic extracts were dried (MgSO$_4$) and were concentrated to provide the title compound (11.8 g, 100%) as a pale yellow foam. ESMS: M+H=276.

c). 5-Bromo-2-chloro-N-(2-hydroxyimino-ethyl)-benzamide

To a solution of 5-bromo-2-chloro-N-(2-oxo-ethyl)-benzamide (11.8 g, 42.5 mmol) in MeOH (400 mL) was added hydroxylamine hydrochloride (5.9 g, 85 mmol) and sodium acetate (6.97 g, 85 mmol). The mixture was stirred 18 h and the MeOH was removed in vacuo. The residue was washed with water and was dried in vacuo for 18 h and used without further purification to provide the title compound (11.7 g, 94%) as a white solid. ESMS: M+H=291.

d). 5-Bromo-2-chloro-N-(2-hydroxyamino-ethyl)-benzamide

To a solution of 5-bromo-2-chloro-N-(2-hydroxyimino-ethyl)-benzamide (2 g, 6.9 mmol) in MeOH (75 mL) under an argon atmosphere at 0° C. was added methyl orange (trace) followed by a saturated solution of MeOH/HCl until a persistent red color was observed. Sodium cyanoborohydride (0.52 g, 8.2 mmol) was dissolved in MeOH (10 mL) and was added sequentially with saturated MeOH/HCl over 0.5 h. The reaction mixture was stirred an additional 2 h and the MeOH was removed in vacuo. The residue was basidified with saturated Na$_2$CO$_3$ and extracted (7×25 mL) with dichloromethane/MeOH (9:1). The combined organic extracts were washed with brine, were dried (Na$_2$SO$_4$) and were concentrated to provide the title compound (0.7 g, 35%) as a white solid. ESMS: M+H=293.

e). 5-Bromo-2-chloro-N-[2-(N-formyl-N-hydroxy-amino)-ethyl]-benzamide

A mixture of acetic anhydride (2 mL) and formic acid (1 mL) was allowed to stand at 55° C. for 2.5 h. After cooling to 0° C., the resulting mixed anhydride (0.5 mL) was added to a solution of 5-bromo-2-chloro-N-(2-hydroxyamino-ethyl)-benzamide (0.7 g, 2.4 mmol) in pyridine (6 mL) at 0° C. under an argon atmosphere. The reaction mixture was stirred for 1 h and the pyridine removed in vacuo. The residue was chased twice with water and twice with MeOH. The resulting solid was washed with ether/acetonitrile (9:1) to provide the title compound (0.42 g, 55%) as a white solid. $^1$H NMR* (400 MHz, CD$_3$OD): δ 8.35 (s, 0.5H); 7.95 (s, 0.5H); 7.58 (m, 2H); 7.38 (m, 1H); 3.78 (m, 1H); 3.73 (m, 1H); 3.62 (m, 2H). * 1:1 mixture of rotamers. ESMS: M+H=321.

The following compounds were prepared in a similar manner to the above examples:

EXAMPLE 5

3,4-Dichloro-N-[2-(N-formyl-N-hydroxy-amino)-ethyl]-benzamide $^1$H NMR* (400 MHz, CD$_3$OD): δ 8.35 (s, 0.5H); 7.99 (dd, j=1.9 and 5.9 Hz, 1H); 7.91 (s, 0.5H); 7.75 (m, 1H); 7.65 (dd, j=3.7 and 8.3 Hz, 1H); 3.83 (m, 1H); 3.76 (m, 1H); 3.69 (m, 2H). * 1:1 mixture of rotamers. ESMS: M+H=277.

EXAMPLE 6

3-Trifluoromethyl-N-[2-(N-formyl-N-hydroxy-amino)-ethyl]-benzamide $^1$H NMR* (400 MHz, CD$_3$OD): δ 8.32 (s, 0.5H); 8.13 (d, j=5.4 Hz, 1H); 8.06 (t, j=7.0 Hz, 1H); 7.89 (s, 0.5H); 7.58 (m, 2H); 7.85 (m, 1H); 7.67 (m, 1H); 3.80 (m, 1H); 3.74 (m, 1H); 3.66 (m, 2H). * 1:1 mixture of rotamers. ESMS: M+H=277.

EXAMPLE 7

2-Methoxy-N-[2-(N-formyl-N-hydroxy-amino)-ethyl]-benzamide $^1$H NMR* (400 MHz, CD$_3$OD): δ 8.36 (s, 0.5H); 7.93 (m, 1.5H); 7.51 (m, 1H); 7.14 (m, 1H); 7.06 (m, 1H); 3.97 (s, 3H); 3.82 (m, 1H); 3.69–3.77 (m, 2H). * 1:1 mixture of rotamers. ESMS: M+H=239.

EXAMPLE 8

N-[2-(N-formyl-N-hydroxy-amino)-ethyl]-thiophen-2-yl-carboxamide $^1$H NMR* (400 MHz, CD$_3$OD): δ 8.30 (s, 0.5H); 7.88 (d, j=5.3 Hz, 0.5H); 7.64 (m, 2H); 7.15 (m, 1H); 3.76 (m, 1H); 3.70 (m, 1H); 3.61 (m, 2H). * 1:1 mixture of rotamers. ESMS: M+H=215.

EXAMPLE 9

N-[2-(N-Formyl-N-hydroxy-amino)-ethyl]-thiophen-3-yl-carboxamide $^1$H NMR* (400 MHz, CD$_3$OD): δ 8.30 (s, 0.5H); 8.03 (m, 1H); 7.87 (d, j=5.7 Hz, 0.5H); 7.46 (m, 2H); 3.76 (m, 1H); 3.70 (m, 1H); 3.61 (m, 2H). * 1:1 mixture of rotamers. ESMS: M+H=215.

EXAMPLE 10

N-[2-(N-Formyl-N-hydroxy-amino)-ethyl]-benzamide $^1$H NMR* (400 MHz, CD$_3$OD): δ 8.34 (s, 0.5H); 7.90 (s, 0.5H); 7.82 (m, 2H); 7.52 (m, 1H); 7.47 (m, 2H); 3.81 (m, 1H); 3.74 (m, 1H); 3.66 (m, 2H). * 1:1 mixture of rotamers. ESMS: M+H=209.

EXAMPLE 11

3-Chloro-N-[2-(N-formyl-N-hydroxy-amino)-ethyl]-thiophen-2-yl-carboxamide $^1$H NMR* (400 MHz, CD$_3$OD): δ 8.35 (s, 0.5H); 7.95 (s, 0.5H); 7.70 (m, 1H); 7.07 (m, 1H); 3.78 (m, 1H); 3.74 (m, 1H); 3.61 (m, 2H). * 1:1 mixture of rotamers. ESMS: M+H=249.

EXAMPLE 12

5-Chloro-N-[2-(N-formyl-N-hydroxy-amino)-ethyl]-thiophen-2-yl-carboxamide $^1$H NMR* (400 MHz, CD$_3$OD): δ 8.30 (s, 0.5H); 7.87 (s, 0.5H); 7.47 (m, 1H); 7.00 (m, 1H); 3.75 (m, 1H); 3.68 (m, 1H); 3.58 (m, 2H). * 1:1 mixture of rotamers. ESMS: M+H=249.

EXAMPLE 13

3,5-Dichloro-N-[2-(N-formyl-N-hydroxy-amino)-ethyl]-benzamide $^1$H NMR* (400 MHz, CD$_3$OD): δ 8.32 (s, 0.5H); 7.89 (s, 0.5H); 7.76 (dd, j=1.9 and 7.3 Hz, 2H); 7.62 (d, j=5.9 Hz, 1H); 3.77 (m, 1H); 3.70 (m, 1H); 3.63 (m, 2H). * 1:1 mixture of rotamers. ESMS: M+H=277.

EXAMPLE 14

3-Chloro-2-fluoro-5-trifluoromethyl-N-[2-(N-formyl-N-hydroxy-amino)-ethyl]-benzamide $^1$H NMR* (400 MHz, CD$_3$OD): δ 8.34 (s, 0.5H); 7.93–8.01 (m, 2.5H); 7.58 (m, 2H); 7.38 (m, 1H); 3.81 (m, 1H); 3.73 (m, 1H); 3.67 (m, 2H). * 1:1 mixture of rotamers. ESMS: M+H=329.

EXAMPLE 15

2-Chloro-5-trifluoromethyl-N-[2-(N-formyl-N-hydroxy-amino)-ethyl]-benzamide $^1$H NMR* (400 MHz, CD$_3$OD): δ 8.35 (s, 0.5H); 7.96 (s, 0.5H); 7.65–7.87 (m, 3H); 7.38 (m, 1H); 3.83 (m, 1H); 3.76 (m, 1H); 3.65 (m, 2H). * 1:1 mixture of rotamers. ESMS: M+H=311.

EXAMPLE 16

3-Phenoxy-N-[2-(N-formyl-N-hydroxy-amino)-ethyl]-benzamide $^1$H NMR* (400 MHz, CD$_3$OD): δ 8.30 (s, 0.5H); 7.87 (s, 0.5H); 7.53 (m, 1H); 7.35–7.44 (m, 4H); 7.08 (m, 2H); 7.05 (m, 2H); 3.76 (m, 1H); 3.69 (m, 1H); 3.62 (m, 2H). * 1:1 mixture of rotamers. ESMS: M+H=301.

EXAMPLE 17

2,6-Dichloro-N-[2-(N-formyl-N-hydroxy-amino)-ethyl]-benzamide $^1$H NMR* (400 MHz, CD$_3$OD): δ 8.92 (br s, 1H); 8.32 (s, 0.5H); 7.95 (s, 0.5H); 7.35–7.44 (m, 4H); 3.80 (m, 1H); 3.69 (m, 1H); 3.66 (t, j=3.2 Hz, 2H). * 1:1 mixture of rotamers. ESMS: M+H=277.

EXAMPLE 18

6-Methoxy-2,3,5-trichloro-N-[2-(N-formyl-N-hydroxy-amino)-ethyl]-benzamide $^1$H NMR* (400 MHz, CD$_3$OD): δ 8.37 (s, 0.5H); 7.97 (s, 0.5H); 7.75 (s, 1H); 3.90 (s, 3H); 3.75–3.90 (m, 2H); 3.67 (m, 2H). * 1:1 mixture of rotamers. ESMS: M+H=341.

EXAMPLE 19

5-Phenoxy-2-chloro-N-[2-(N-formyl-N-hydroxy-amino)-ethyl]-benzamide

5-Phenoxy-2-chloro-N-[2-(N-formyl-N-hydroxy-amino)-ethyl]-benzamide was prepared from 2-chloro-5-phenoxybenzoic acid in a similar manner to the above examples.

¹H NMR* (400 MHz, CD$_3$OD): δ 8.30 (s, 0.5H); 7.93 (s, 0.5H); 7.38–7.42 (m, 3H); 7.17 (t, j=7.3 Hz, 1H); 7.00–7.07 (m, 4H); 3.76 (m, 1H); 3.71 (m, 1H); 3.59 (t, j=5.9 Hz, 2H). * 1:1 mixture of rotamers. ESMS: M+H=335.

EXAMPLE 20

2-Chloro-5-phenoxybenzoic acid

A mixture of 2-chloro-5-hydroxybenzoic acid (0.52 g, 3.0 mmol), phenyl boronic acid trimeric anhydride (1.6 g, 5 mmol), copper (II) acetate (0.55 g, 3.0 mmol), triethylamine (1.5 g, 15 mmol), pyridine (1.2 g; 15 mmol) and 4 angstrom sieves (2.6 g) were strirred in dichloromethane (15 mL) for 18 h. The mixture was acidified with 3N HCl and was extracted with diethyl ether (3×). The combined organic extracts were washed with brine, were dried (MgSO$_4$) and were concentrated. The residue was purified by flash column chromatography (silica gel, 10% methanol/chloroform with 1% formic acid) to provide the title compound as a brown solid (0.3 g, 40%). ESMS: M+H=249.

EXAMPLE 21

2-Chloro-5-benzyloxy-N-[2-(N-formyl-N-hydroxy-amino)-ethyl]-benzamide

¹H NMR* (400 MHz, CD$_3$OD): δ 8.34 (s, 0.5H); 7.95 (s, 0.5H); 7.30–7.44 (m, 6H); 7.05–7.09 (m, 2H); 5.09 (s, 2H); 3.76 (m, 1H); 3.69 (m, 1H); 3.62 (m, 2H). * 1:1 mixture of rotamers. ESMS: M+H=349.

EXAMPLE 22

2-Chloro-5-methoxy-N-[2-(N-formyl-N-hydroxy-amino)-ethyl]-benzamide

¹H NMR* (400 MHz, CD$_3$OD): δ 8.35 (s, 0.5H); 7.95 (s, 0.5H); 7.31–7.35 (m, 1H); 6.98–7.01 (m, 2H); 3.81 (s, 3H); 3.78 (m, 1H); 3.70 (m, 1H); 3.62 (m, 2H). * 1:1 mixture of rotamers. ESMS: M+H=273.

EXAMPLE 23

2-Chloro-5-hydroxy-N-[2-(N-formyl-N-hydroxy-amino)-ethyl]-benzamide

¹H NMR* (400 MHz, CD$_3$OD): δ 8.34 (s, 0.5H); 7.94 (s, 0.5H); 7.19–7.24 (m, 1H); 6.81–6.85 (m, 2H); 3.78 (m, 1H); 3.75 (m, 1H); 3.60 (m, 2H). * 1:1 mixture of rotamers. ESMS: M+H=259.

EXAMPLE 24

6-Hydroxy-2,3,5-trichloro-N-[2-(N-formyl-N-hydroxy-amino)-ethyl]-benzamide

¹H NMR* (400 MHz, CD$_3$OD): δ 8.35 (s, 0.5H); 7.97 (s, 0.5H); 7.61 (s 1H); 3.74–3.79 (m 2H); 3.60 (m, 2H). * 1:1 mixture of rotamers. ESMS: M+H=327.

EXAMPLE 25

5-Chloro4-[2-(N-formyl-N-hydroxy-amino)-ethyl] amido-benzimidazole

¹H NMR* (400 MHz, CD$_3$OD): δ 8.40 (s, 0.5H); 8.30 (d, j=5.5 Hz, 1H); 8.04 (s, 0.5H); 7.66 (d, j=8.0 Hz, 1H); 7.37 (d, j=8.6 Hz, 1H); 3.89–3.92 (m, 1H); 3.82–3.85 (m, 1H); 3.73–3.78 (m, 2H). * 1:1 mixture of rotamers. ESMS: M+H=283.

With appropriate manipulation and protection of any chemical functionality, synthesis of the remaining compounds of Formula (I) is accomplished by methods analogous to those above and to those described in the Experimental section.

In order to use a compound of the Formula (I) or a pharmaceutically acceptable salt thereof for the treatment of humans and other mammals it is normally formulated in accordance with standard pharmaceutical practice as a pharmaceutical composition.

The present compounds are useful for the treatment of bacterial infections including but not limited to respiratory tract infections and/or Gram positive infections.

Compounds of Formula (I) and their pharmaceutically acceptable salts may be administered in a standard manner for antibiotics, for example orally, parenterally, sublingually, dermally, transdermally, rectally, via inhalation or via buccal administration.

Compositions of Formula (I) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula(I) or a pharmaceutically acceptable salt thereof calculated as the free acid. Each dosage unit for intranasal administration contains suitably 1–400 mg and preferably 10 to 200 mg per person. A topical formulation contains suitably 0.01 to 5.0% of a compound of Formula (I).

The daily dosage regimen for oral administration is suitably about 0.01 mg/Kg to 40 mg/Kg, of a compound of Formula(I) or a pharmaceutically acceptable salt thereof calculated as the free acid. The daily dosage regimen for parenteral administration is suitably about 0.001 mg/Kg to 40 mg/Kg, of a compound of Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (I) are demonstrated by the following test:

Biological Assay

S. aureus or E. coli PDF activity is measured at 25° C., using a continuous enzyme-linked assay developed by Lazennec & Meinnel, (1997) "Formate dehydrogenase-coupled spectrophotometric assay of peptide deformylase" Anal. Biochem. 244, pp. 180–182, with minor modifications. The reaction mixture is contained in 50 uL with 50 mM potassium phosphate buffer (pH7.6), 15 mM NAD, 0.25 U formate dehydrogenase. The substrate peptide, f-Met-Ala-Ser, is included at the $K_M$ concentration. The reaction is triggered with the addition of 10 nM Def1 enzyme, and absorbance is monitored for 20 min at 340 nm.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: Staphylococcus aureus Oxford, Streptococcus pneumoniae R6, Streptococcus pyogenes CN10, Enterococcus faecalis I, Haemophilus influenzae Q1, Escherichia coli DC0, E. coli EES, E. coli 7623 (AcrAB+) E. coli 120 (AcrAB−) Klebsiella pneumoniae E70, Pseudomonas aeruginosa K799wt and Candida albicans GRI 681. The minimum inhibitory concentration (MIC) was determined as the lowest concentration of compound that inhibited visible growth. A mirror reader was used to assist in determining the MIC endpoint.

All publications, including but not limited to patents and patent applications cited in this specification are herein incorporated by reference as if each individual publication were specifically and individually indicated to be incorporated by reference as though fully set forth.

What is claimed is:

1. A compound according to formula (I):

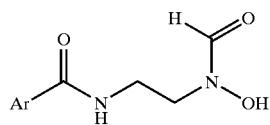

(I)

wherein:

Ar is an aryl group selected from the group consisting of phenyl, azaindolyl, pyridyl, indolyl, quinolinyl, pyrazinyl, benzenethiophenyl, isoxazolyl, isoquinolinyl, napthyl, oxazolyl, isothiazolyl, benzothiaphenyl, furyl, pyridazinyl, thienyl, benzofuryl, triazolyl, imidazolyl, and thiazolyl; such that Ar may be optionally substituted with one, two, or three substituents selected from the group consisting of optionally substituted alkyl or cycloalkyl of one to nine carbons, halo, alkoxy of one to nine carbons, hydroxy, amino, hydroxyalkyl of one to nine carbons, alkoxyalkyl, wherein the alkyl and alkylene groups are independently of one to nine carbons, optionally substituted aryl or optionally substituted heteroaryl, carboxy, and alkoxycarbonyl.

2. A compound according to claim 1 selected from the group consisting of:

3,4-Dichloro-N-[2-(N-formyl-N-hydroxy-amino)-ethyl]-benzamide;

3-Trifluoromethyl-N-[2-(N-formyl-N-hydroxy-amino)-ethyl]-benzamide;

2-Methoxy-N-[2-(N-formyl-N-hydroxy-amino)-ethyl]-benzamide;

N-[2-(N-Formyl-N-hydroxy-amino)-ethyl]-thiophen-2-yl-carboxamide;

N-[2-(N-Formyl-N-hydroxy-amino)-ethyl]-thiophen-3-yl-carboxamide;

N-[2-(N-Formyl-N-hydroxy-amino)-ethyl]-benzamide;

3-Chloro-N-[2-(N-formyl-N-hydroxy-amino)-ethyl]-thiophen-2-yl-carboxamide;

5-Chloro-N-[2-(N-formyl-N-hydroxy-amino)-ethyl]-thiophen-2-yl-carboxamide;

3,5-Dichloro-N-[2-(N-formyl-N-hydroxy-amino)-ethyl]-benzamide;

3-Chloro-2-fluoro-5-trifluoromethyl-N-[2-(N-formyl-N-hydroxy-amino)-ethyl]-benzamide;

2-Chloro-5-trifluoromethyl-N-[2-(N-formyl-N-hydroxy-amino)-ethyl]-benzamide;

3-Phenoxy-N-[2-(N-formyl-N-hydroxy-amino)-ethyl]-benzamide;

2,6-Dichloro-N-[2-(N-formyl-N-hydroxy-amino)-ethyl]-benzamide;

6-Methoxy-2,3,5-trichloro-N-[2-(N-formyl-N-hydroxy-amino)-ethyl]-benzamide;

5-Phenoxy-2-chloro-N-[2-(N-formyl-N-hydroxy-amino)-ethyl]-benzamide;

2-Chloro-5-phenoxybenzoic acid;

2-Chloro-5-benzyloxy-N-[2-(N-formyl-N-hydroxy-amino)-ethyl]-benzamide;

2-Chloro-5-methoxy-N-[2-(N-formyl-N-hydroxy-amino)-ethyl]-benzamide;

2-Chloro-5-hydroxy-N-[2-(N-formyl-N-hydroxy-amino)-ethyl]-benzamide;

6-Hydroxy-2,3,5-trichloro-N-[2-(N-formyl-N-hydroxy-amino)-ethyl]-benzamide; and

5-Chloro-4-[2-(N-formyl-N-hydroxy-amino)-ethyl]amido-benzimidazole.

3. A compound according to claim 2 selected from the group consisting of:

2,3-Dichloro-N-[2-(N-formyl-N-hydroxy-amino)-ethyl]-benzamide;

2,3,5-Trichloro-N-[2-(N-formyl-N-hydroxy-amino)-ethyl]-benzamide;

2,5-Dichloro-N-[2-(N-formyl-N-hydroxy-amino)-ethyl]-benzamide; and

5-Bromo-2-chloro-N-[2-(N-formyl-N-hydroxy-amino)-ethyl]-benzamide.

4. A method of treating a bacterial infection by administering to a subject a compound according to claim 1.

5. A method according to claim 4 wherein the bacterial infection is a respiratory tract infection or the Gram+ TPP.

* * * * *